United States Patent
Kim et al.

(10) Patent No.: US 7,060,405 B2
(45) Date of Patent: Jun. 13, 2006

(54) NAPHTHOQUINONE DERIVATIVE AND ELECTROPHOTOGRAPHIC PHOTORECEPTOR CONTAINING THE SAME

(75) Inventors: Beom-jun Kim, Gyeonggi-do (KR); Saburo Yokota, Gyeonggi-do (KR); Kyung-yol Yon, Gyeonggi-do (KR); Hwan-koo Lee, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 198 days.

(21) Appl. No.: 10/670,264

(22) Filed: Sep. 26, 2003

(65) Prior Publication Data

US 2004/0156651 A1    Aug. 12, 2004

(30) Foreign Application Priority Data

Feb. 10, 2003    (KR) ...................... 10-2003-0008144

(51) Int. Cl.
*G03G 5/06*    (2006.01)
*C07C 50/38*    (2006.01)

(52) U.S. Cl. .................... 430/58.25; 430/72; 399/159; 552/299

(58) Field of Classification Search ................. 430/72, 430/58.25; 399/159; 552/299
See application file for complete search history.

(56) References Cited

U.S. PATENT DOCUMENTS

| 5,977,389 A | 11/1999 | Okada et al. |
| 5,994,012 A | 11/1999 | Watanabe et al. |
| 6,063,534 A | 5/2000 | Hamasaki |
| 6,797,444 B1 * | 9/2004 | Itami ........................ 430/58.2 |

FOREIGN PATENT DOCUMENTS

JP    2000-314969    11/2000

OTHER PUBLICATIONS

Japanese Patent Office Action for corresponding Japanese Patent application No. 2004-33856 dated Oct. 17, 2005.

* cited by examiner

*Primary Examiner*—John L Goodrow
(74) *Attorney, Agent, or Firm*—Staas & Halsey LLP

(57) ABSTRACT

A naphthoquinone derivative is utilized in an electrophotographic photoreceptor as an electron-transporting material. The electrophotographic photoreceptor is improved in terms of solubility in an organic solvent, compatibility with a binder resin, and electron transport capability.

30 Claims, 1 Drawing Sheet

NAPHTHOQUINONE DERIVATIVE AND ELECTROPHOTOGRAPHIC PHOTORECEPTOR CONTAINING THE SAME

CROSS-REFERENCE TO RELATED APPLICATIONS

This application claims the benefit of Korean Application No. 2003-8144, filed Feb. 10, 2003, in the Korean Intellectual Property Office, the disclosure of which is incorporated herein by reference.

BACKGROUND OF THE INVENTION

1. Field of the Invention

The present invention relates to a naphthoquinone derivative and an electrophotographic photoreceptor containing the same. More particularly, the present invention relates to a naphthoquinone derivative and an electrophotographic photoreceptor containing the naphotoquinone derivative which has enhanced solubility in an organic solvent, compatibility with a binder resin, and electron transport capability.

2. Description of the Related Art

Generally, an electrophotographic photoreceptor comprises a conductive substrate and a photosensitive layer on the substrate. The photosensitive layer contains a charge-generating material, a charge-transporting material, and a binder resin.

Electrophotographic photoreceptors are classified into multi-layer photoreceptors and single-layer photoreceptors. The multi-layer photoreceptor has a functionally laminated structure in which the charge-generating material and the charge-transporting material are laminated one onto the other as separate layers. The single-layer photoreceptor has a structure in which the charge-generating material and the charge-transporting material are contained in the same layer. Among them, the multi-layer photoreceptor is mainly used.

On the other hand, attention has been paid to the single-layer photoreceptor because the manufacturing process is relatively simple and the surface of the photoreceptor is positively charged by corona discharge, thus generating a smaller quantity of ozone. Therefore, the study of the single-layer photoreceptor has been actively carried out at present.

Representative examples of the single-layer electrophotographic photoreceptor include a photoreceptor obtained by dispersing a photoconductive phthalocyanine in a resin and a photoreceptor obtained by dispersing an aggregate of thiapyrylium and polycarbonate together with a charge-transporting material in a resin. However, such photoreceptors have poor electrostatic property and restriction selection of suitable photosensitive materials due to an adverse effect of photosensitive materials on the environment. Thus, these photoreceptors are not currently used.

Recently, one of the most widely used single-layer photoreceptors has been a positive charging type photoreceptor having a photosensitive layer obtained by dispersing a charge-generating material, a hole-transporting material, and an electron-transporting material in a binder resin. Such a single-layer photoreceptor has the advantage of allowing a wide selection of materials, because of the separation of functions between the charge-generating material and the charge-transporting material. Also, the charge-generating material may be used in a low concentration, helping to enhance the functional and chemical stability of the photoreceptor.

Among the materials used in such a positive charging type single-layer photoreceptor, the electron-transporting material is considered the most important. Generally, the electron transport capability of the electron-transporting material is more than 100 times smaller than the hole transport capability of the hole-transporting material. Accordingly, the performance of a single-layer photoreceptor depends on the electron transport capability of the electron-transporting material.

Methods to manufacture an organic photoreceptor with a prolonged life using a diphenoquinone derivative, a stilbenequinone derivative, or a naphthoquinone derivative as an electron-transporting material are disclosed in U.S. Pat. Nos. 5,994,012; 6,063,534; and 5,977,389, respectively. However, when such a diphenoquinone derivative is used as an electron-transporting material, electron transport capability becomes poor. Therefore, an organic photoreceptor comprising such a diphenoquinone derivative has problems such as a decrease of a charge potential and an increase of an exposure potential when used repeatedly. On the other hand, when such a stilbenequinone derivative or naphthoquinone derivative is used as an electron-transporting material, solubility in an organic solvent, compatibility with a binder resin, and electron transport capability are not satisfactory.

SUMMARY OF THE INVENTION

The present invention provides a new electron-transporting material that overcomes the above and/or other problems.

The present invention also provides an electrophotographic photoreceptor comprising the electron-transporting material, which is improved in terms of solubility in an organic solvent, compatibility with a binder resin, and transport of electrons.

According to an aspect of the present invention, a naphthoquinone derivative may be represented by the Formula 1:

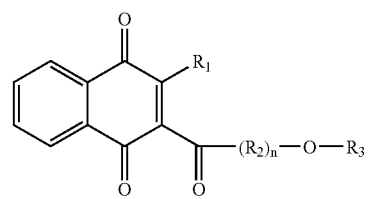

Formula 1 wherein:

$R_1$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms;

$R_2$ is selected from the group consisting of an alkylene group having 2 to 20 carbon atoms, an arylene group having 6 to 30 carbon atoms, and an arylene-alkylene group having 7 to 30 carbon atoms;

n is 0 or 1; and $R_3$ is selected from the group consisting of a substituted or unsubstituted alkyl group having 1 to 20 carbon atoms, a substituted or unsubstituted aryl group having 6 to 30 carbon atoms, a substituted or unsubstituted aralkyl group having 7 to 30 carbon atoms, and a group represented by Formula 1a or 1b:

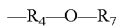
—R₄—O—R₇          Formula 1a

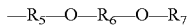
—R₅—O—R₆—O—R₇          Formula 1b wherein:

$R_4$, $R_5$, and $R_6$ are selected from the group consisting of, independently, an alkylene group having 2 to 20 carbon atoms, an arylene group having 6 to 30 carbon atoms, and an arylene-alkylene group having 7 to 30 carbon atoms; and $R_7$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms, wherein the naphthoquinone derivatives having the Formula 1, where n=0, $R_3$ is a substituted or unsubstituted alkyl group having 1 to 20 carbon atoms, a substituted or unsubstituted aryl group having 6 to 30 carbon atoms, or a substituted or unsubstituted aralkyl group having 7 to 30 carbon atoms, are excluded.

According to another aspect of the present invention, an electrophotographic photoreceptor comprises a substrate and a photosensitive layer formed on the substrate. The photosensitive layer includes a naphthoquinone derivative.

According to another aspect of the present invention, the electrophotographic photoreceptor is utilized in an image forming apparatus, an electrophotgraphic drum, or an electrophographic cartridge in accordance with selected embodiments of the present invention.

Additional aspects and advantages of the invention will be set forth in part in the description which follows and, in part, will be obvious from the description, or may be learned by practice of the invention.

BRIEF DESCRIPTIONS OF THE DRAWINGS

These and/or other aspects and advantages of the invention will become apparent and more readily appreciated from the following description of the preferred embodiments taken in conjunction with the accompanying drawings, of which:

DETAILED DESCRIPTION OF THE PREFERRED EMBODIMENTS

Figure 1:
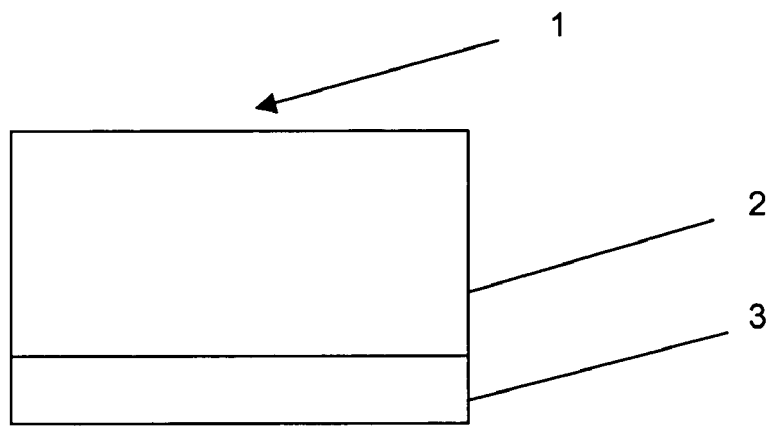
FIG. 1 is a block diagram illustrating (not to scale) an electrophotographic photoreceptor installed on a conductive substrate in accordance with the present invention.

Reference will now be made in detail to the present preferred embodiments of the present invention, examples of which are illustrated in the accompanying drawings, wherein like reference numerals refer to the like elements throughout. The embodiments are described below in order to explain the present invention by referring to the figures.

Hereinafter, the present invention will be described in more detail.

The naphthoquinone derivative as defined in Formula 1 has a naphthoquinone structure including a flexible ether group. Due to the structural characteristics of the naphthoquinone derivative, an electrophotographic photoreceptor using the naphthoquinone derivative is improved in terms of solubility in an organic solvent, compatibility with a binder resin, and electron transport capability.

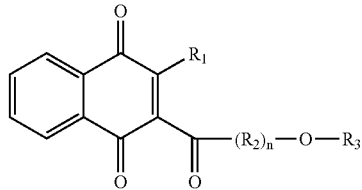

Formula 1 wherein:

$R_1$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms;

$R_2$ is selected from the group consisting of an alkylene group having 2 to 20 carbon atoms, an arylene group having 6 to 30 carbon atoms, and an arylene-alkylene group having 7 to 30 carbon atoms;

n is 0 or 1; and $R_3$ is selected from the group consisting of a substituted or unsubstituted alkyl group having 1 to 20 carbon atoms, a substituted or unsubstituted aryl group having 6 to 30 carbon atoms, a substituted or unsubstituted aralkyl group having 7 to 30 carbon atoms, and a group represented by Formula 1a or 1b:

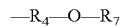
—R₄—O—R₇          Formula 1a

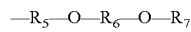
—R₅—O—R₆—O—R₇          Formula 1b wherein:

$R_4$, $R_5$, and $R_6$ are selected from the group consisting of, independently, an alkylene group having 2 to 20 carbon atoms, an arylene group having 6 to 30 carbon atoms, and an arylene-alkylene group having 7 to 30 carbon atoms; and $R_7$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms, wherein the naphthoquinone derivatives having the Formula 1, where n=0, $R_3$ is a substituted or unsubstituted alkyl group having 1 to 20 carbon atoms, a substituted or unsubstituted aryl group having 6 to 30 carbon atoms, or a substituted or unsubstituted aralkyl group having 7 to 30 carbon atoms, are excluded.

Preferably, the naphthoquinone derivative as defined in Formula 1 is selected from compounds represented by Formulas 2 to 16.

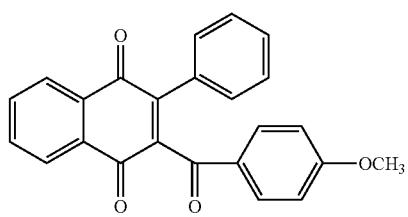

Formula 2

Formula 3
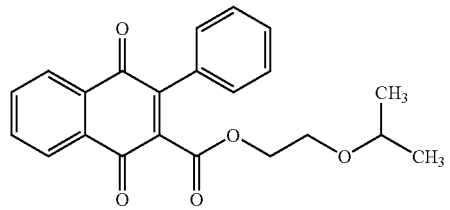
Formula 4
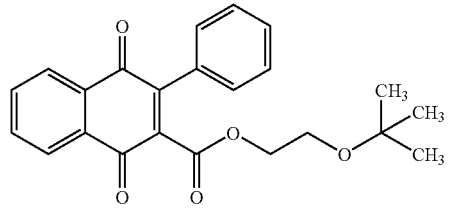
Formula 5
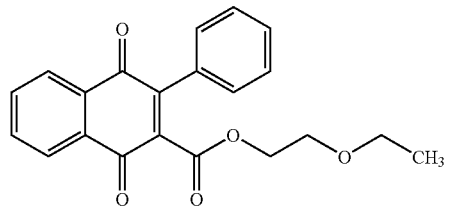
Formula 6
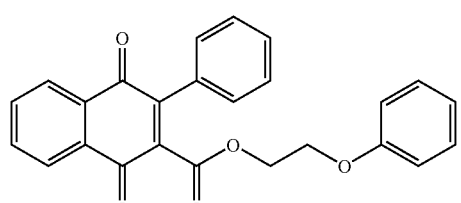
Formula 7
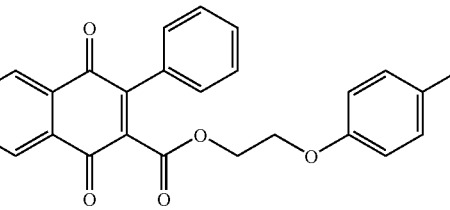
Formula 8
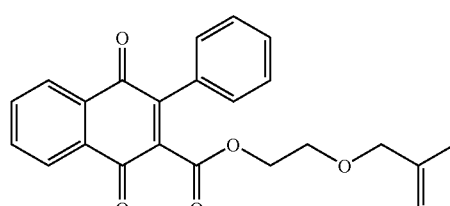
Formula 9
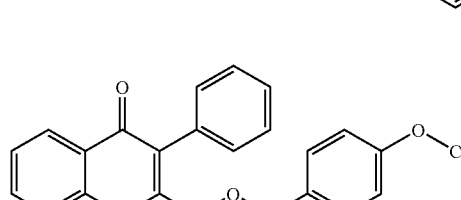
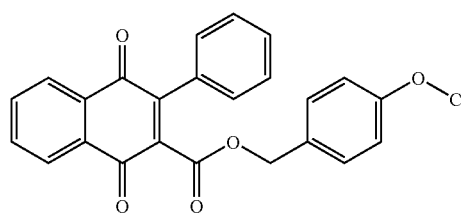
Formula 10
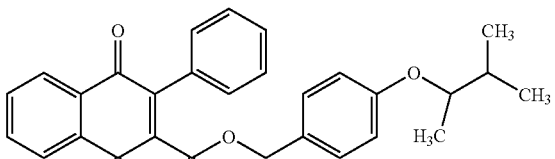
Formula 11
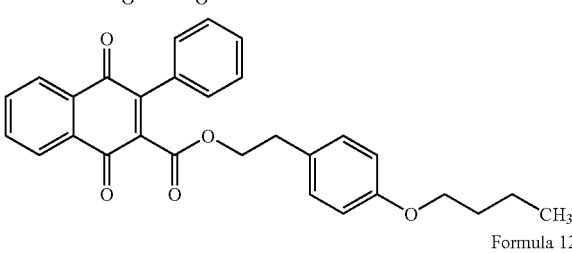
Formula 12
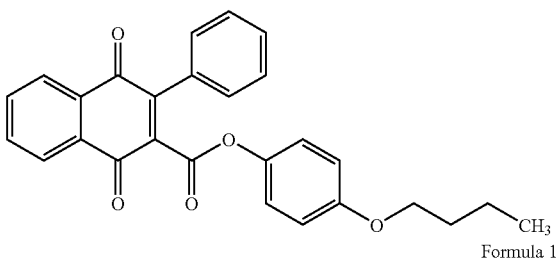
Formula 13
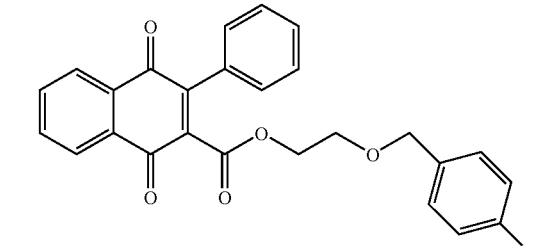
Formula 14
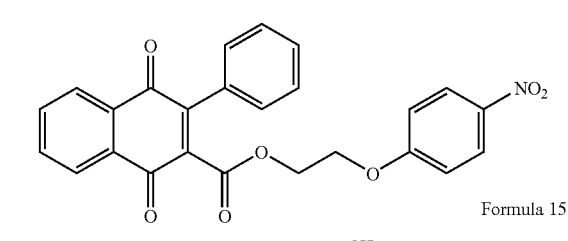
Formula 15
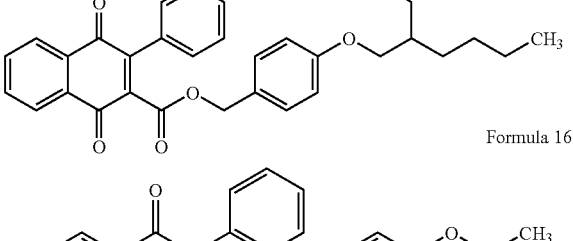
Formula 16
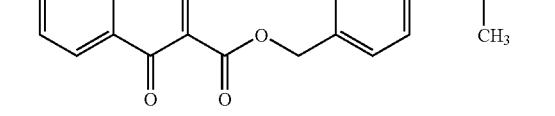

A compound of Formula 2 is the naphthoquinone derivative wherein n is 1, $R_2$ is a phenylene group and $R_3$ is a methyl group. Compounds of Formulas 3, 4, 5, 6, 7, 8, 13, and 14 are the naphthoquinone derivatives wherein n is 0, $R_3$ is —$R_4$—O—$R_7$ of Formula 1a where $R_4$ is an ethylene group and $R_7$ is selected from the group consisting of an isopropyl, a tert-butyl, an ethyl, a phenyl, a 4-tert-butylphenyl, a benzyl, a 4-nitrophenylmethyl, and a 4-nitrophenyl group, respectively.

A compound of the Formula 12 is a naphthoquinone derivative wherein n is 0, $R_3$ is —$R_4$—O—$R_7$ of Formula 1a, $R_4$ is a phenyl group and $R_7$ is a butyl group.

Compounds of Formulas 9, 10, 15, and 16 are the naphthoquinone derivatives wherein n is 0, $R_3$ is —$R_4$—O—$R_7$ of Formula 1a where $R_4$ is a methylene-phenylene group and $R_7$ is selected from the group consisting of a methyl group, —$CH(CH_3)CH(CH_3)_2$, —$CH_2CH(C_2H_5)(CH_2)_3CH_3$, and an isopropyl group, respectively.

A compound of Formula 11 is the naphthoquinone derivative wherein n is 0, $R_3$ is —$R_4$—O—$R_7$ of Formula 1a where $R_4$ is an ethylene-phenylene group and $R_7$ is an n-butyl group.

Hereinafter, an organic photoreceptor using the naphthoquinone derivative as defined above will be described.

Generally, an electrophotographic photoreceptor comprises a conductive substrate and a photosensitive layer which is coated on the substrate. Generally, a drum or a belt made of metal or plastic is used as the conductive substrate.

As mentioned above, an electrophotographic photoreceptor is classified as a multi-layer photoreceptor or a single-layer photoreceptor. The multi-layer photoreceptor has a charge-generating layer that includes a charge-generating material and a charge-transporting layer that includes a charge-transporting material as separate layers. In the single-layer photoreceptor, a charge-generating material and a charge-transporting material are located in the same layer.

The naphthoquinone derivative as defined in the Formula 1 acts as a charge-transporting material, and preferably an electron-transporting material. Thus, in the multi-layer photoreceptor, the naphthoquinone derivative is included in a charge-transporting layer. On the other hand, in the single-layer photoreceptor, the naphthoquinone derivative is included in a single photosensitive layer containing a charge-generating material.

Examples of the charge-generating material as used herein include, but are not limited to, an organic material such as phthalocyanine pigment, azo pigment, quinone pigment, perylene pigment, indigo pigment, bisbenzoimidazole pigment, quinacridone pigment, azulenium dye, squarylium dye, pyrylium dye, triarylmethane dye, and cyanine dye; and an inorganic material such as amorphous silicone, amorphous selenium, trigonal selenium, tellurium, selenium-tellurium alloy, cadmium sulfide, antimony sulfide, and zinc sulfide. The aforementioned charge-generating materials may be used alone or in combination.

In the case of the multi-layer photoreceptor, the charge-generating material is dispersed in a solvent together with a binder resin. Then, the mixture is applied to the substrate by coating, vacuum deposition, sputtering, or chemical vapor deposition (CVD) to form a charge-generating layer. The thickness of the charge-generating layer is 0.1 to 1.0 µm.

Preferably, an insulating polymer is used as the binder resin. Examples of the insulating polymer include, but are not limited to, polycarbonate, polyester, methacryl resin, acryl resin, polyvinylchloride, polyvinylidenechloride, polystyrene, polyvinylacetate, silicone resin, silicone-alkyd resin, styrene-alkyd resin, poly-N-vinylcarbazole, phenoxy resin, epoxy resin, polyvinylbutyral, polyvinylacetal, polyvinylformal, polysulfone, polyvinylalcohol, ethyl cellulose, phenol resin, polyamide, carboxy-methyl cellulose, and polyurethane. The insulating polymers may be used alone or in combination.

In the multi-layer photoreceptor, a charge-transporting layer containing the naphthoquinone derivative of Formula 1 is formed on the charge-generating layer. Alternatively, the charge-generating layer may also be formed on the charge-transporting layer. To form the charge-transporting layer, the naphthoquinone derivative of Formula 1 and the binder resin are dissolved in a solvent, and the mixture is applied to the charge-generating layer.

In the single-layer photoreceptor, the charge-generating material, the binder resin, and the charge-transporting material are dispersed in a solvent and the mixture is applied to the substrate. As a result, a photosensitive layer is formed. In this embodiment, the naphthoquinone derivative of Formula 1 is used as the charge-transporting material. However, the naphthoquinone derivative may be used in combination with a separate charge-transporting material. Generally, a charge-transporting material has a hole-transporting material and an electron-transporting material. Preferably, in a single-layer photoreceptor, a hole-transporting material is used together with the naphthoquinone derivative.

Examples of the hole-transporting material to be used together with the naphthoquinone derivative of Formula 1 include, but are not limited to, a nitrogen-containing cyclic compound or a condensed polycyclic compound such as pyrenes, carbazoles, hydrazones, oxazoles, oxadiazoles, pyrazolines, arylamines, arylmethanes, benzidines, thiazoles, and styryls. A high molecular weight compound or a polysilane compound with a main or side chain group may be used to substitute the aforementioned hole-transporting materials.

Examples of the separate electron-transporting material to be used together with the naphthoquinone derivative of Formula 1 include, but are not limited to, an electron-withdrawing low molecular weight compound such as benzoquinones, cyanoethylenes, cyanoquinodimethanes, fluorenones, xantones, phenanthraquinones, phthalic anhydrides, thiopyranes, and diphenoquinones. An electron-transporting, high molecular weight compound or a pigment with n-type semiconductor property may also be used.

Each of the aforementioned hole-transporting materials and electron-transporting materials may be used alone or in combination.

Preferably, the thickness of the photosensitive layer ranges from 5 to 50 µm regardless of whether the photoreceptor is a multi-layer photoreceptor or a single-layer photoreceptor.

Examples of the solvent to be used in the formation of the photosensitive layer include an organic solvent such as alcohols, ketones, amides, ethers, esters, sulfones, aromatic hydrocarbons, and halogenated aliphatic hydrocarbons. A coating material for the photosensitive layer may be applied to a substrate by dip coating, ring coating, roll coating, or spray coating.

Preferably, the binder resin is added in an amount of 0.5 to 2 parts by weight based on 1 part by weight of the charge-transporting material. If the content of the binder resin is less than 0.5 parts by weight, the mechanical strength of the photosensitive layer is lowered due to the insufficient content of the binder resin. On the other hand, if the content of the binder resin exceeds 2 parts by weight, charge transport capability is decreased, and thus photosensitivity is decreased. As a result, a residual potential is increased.

The photoreceptor of the present invention may further comprise a conductive layer between the substrate and the photosensitive layer. A conductive powder such as carbon black, graphite, metal powder or metal oxide powder is dispersed in a solvent to obtain a dispersion solution. The dispersion solution is coated on the substrate and dried to form the conductive layer. It is preferable to limit the thickness of the conductive layer to a range of 5 to 50 μm.

The photoreceptor of the present invention may further comprise an intermediate layer between the substrate and the photosensitive layer or between the conductive layer and the photosensitive layer. The intermediate layer is used to improve adhesion. Examples of the intermediate layer include, but are not limited to, an anodic layer of aluminum; a resin dispersion layer of metal oxide powder such as titanium oxide and tin oxide; and a resin layer such as polyvinylalcohol, casein, ethylcellulose, gelatin, phenol resin, and polyamide. Preferably, the thickness of the intermediate layer ranges from 0.05 to 5 μm. The binder resin may be used together with an additive such as a plasticizer, a leveling agent, a dispersion stabilizer, an antioxidant, and a light stabilizer.

Examples of the antioxidant include a phenolic compound, a sulfur compound, a phosphorus compound, and an amine compound. Examples of the light stabilizer include a benzotriazole compound, a benzophenone compound, and a hindered amine compound.

The naphthoquinone derivative of Formula 1 is widely used in copying machines, laser printers, Cathode Ray Tube (CRT) printers, light-emitting diode (LED) printers, liquid crystal printers, and a laser electrophotographic field.

The term, "alkyl" as used herein embraces straight or branched radicals having 1 to 20 carbon atoms, and preferably 1 to 12 carbon atoms. Examples of the alkyl include methyl, ethyl, n-propyl, isopropyl, n-butyl, isobutyl, sec-butyl, t-butyl, pentyl, isoamyl, hexyl, and octyl. One or more hydrogen atoms in the alkyl may be substituted with a nitro, a cyano, or a halogen atom.

The term, "aryl" as used herein, which may be used alone or in combination, refers to an aromatic compound having 6 to 30 carbon atoms containing one or more rings. The rings may be attached to each other as a pendant group or may be fused together. The aryl embraces aromatic radicals such as phenyl, naphthyl, tetrahydronaphthyl, and biphenyl. The aryl may have one or five substituents such as hydroxyl, halogen, halide, nitro, cyano, alkoxy, and lower alkylamino.

The term, "aralkyl" as used herein refers to a group in which one or more hydrogen atoms in the aryl as defined above are substituted with lower alkyl such as methyl, ethyl, and propyl. Representative aralkyl is benzyl, phenylethyl, or phenylmethyl.

Hereinafter, the present invention will be described in more detail with reference to examples but is not limited thereto.

EXAMPLE 1

15 parts by weight of a naphthoquinone derivative of Formula 2 as an electron-transporting material, 35 parts by weight of enamine-stilbene of the following Formula 17 as a hole-transporting material, 8 parts by weight of gamma-titanyl phthalocyanine of Formula 18, 60 parts by weight of Z-polycarbonate, 237 parts by weight of methylene chloride, and 158 parts by weight of 1,1,2-trichloroethane were mixed and dispersed using a ball mill to prepare a coating material. The coating material was applied to an aluminum drum with a diameter of 30 mm and dried at 120° C. for 1 hour to prepare a single-layer electrophotographic photoreceptor.

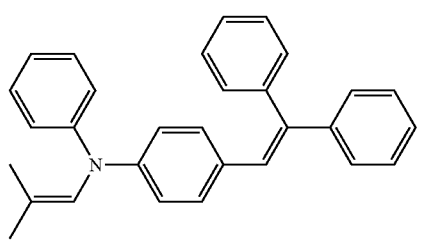

Formula 17

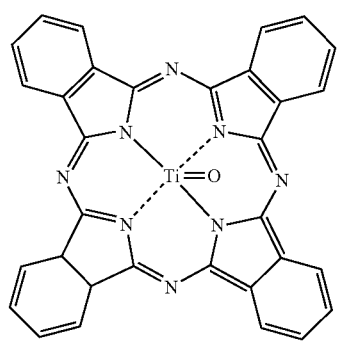

Formula 18

COMPARATIVE EXAMPLE 1

A single-layer electrophotographic photoreceptor was prepared in the same manner as in Example 1 in the absence of an electron-transporting material.

EXPERIMENTS

Electrophotographic characteristics of the photoreceptors of Example 1 and Comparative example 1 were measured using a drum test system (PDT-2000, a product of QEA CO.).

In the case of Comparative Example 1, after 100 cycles, a charge potential was decreased and an exposure potential was increased, compared to their initial values. On the other hand, in the case of Example 1, after 100 cycles, the initial values of a charge potential and an exposure potential were maintained. Thus, the photoreceptor of Example 1 in which the naphthoquinone derivative of Formula 1 is used as an electron-transporting material, is excellent in terms of an electrostatic property.

In addition, two properties of the naphthoquinone derivative of Formula 2 that was used in Example 1 was measured: solubility in an organic solvent and compatibility with a binder resin. It was found that the naphthoquinone derivative provides improved solubility in an organic solvent and compatibility with a binder resin, compared to a conventional electron-transporting material.

As is apparent from the above description, an electrophotographic photoreceptor using the naphthoquinone derivative of the present invention as an electron-transporting material is improved in terms of solubility in an organic solvent, compatibility with a binder resin, and electron transport capability.

FIG. 1 is a block diagram illustrating (not to scale) an electrophotographic photoreceptor 1 comprising an organic photoreceptor 2 installed on a substrate 3 in accordance with an embodiment of the present invention.

Figure 2:
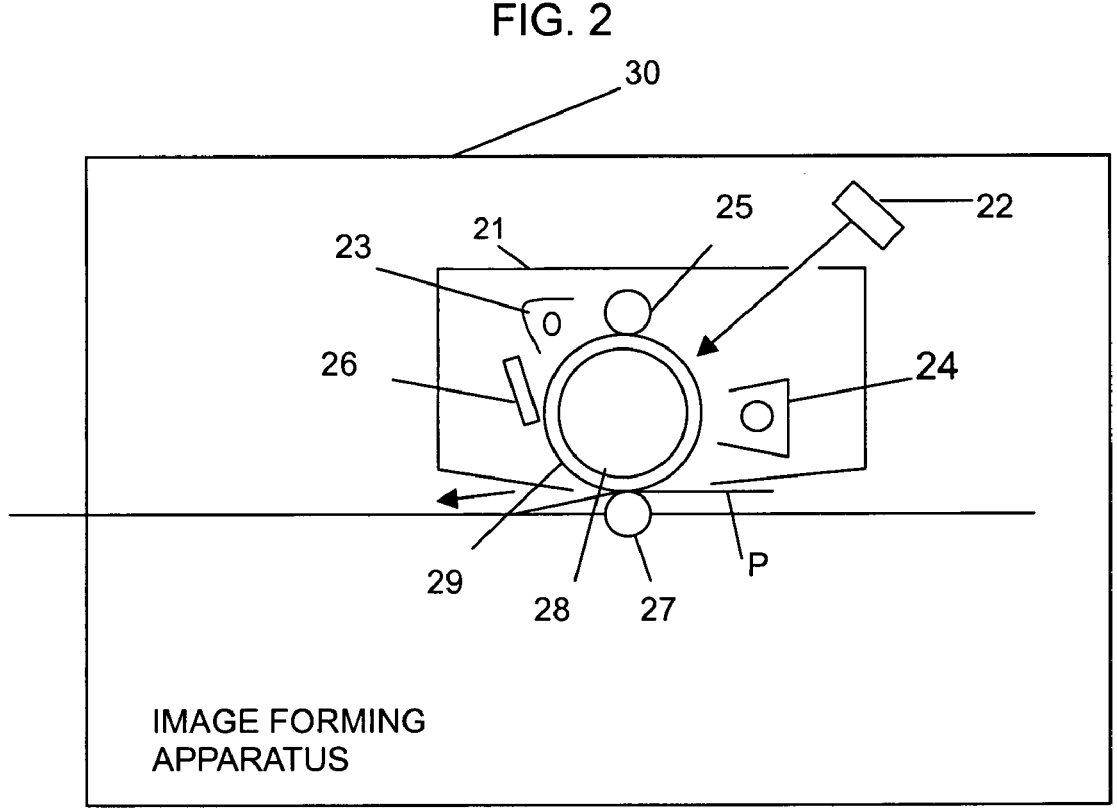
FIG. 2 is a schematic representation of an image forming apparatus, an electrophotgraphic drum, and an electrophographic cartridge in accordance with selected embodiments of the present invention.

FIG. 2 is a schematic representation of an image forming apparatus 30, an electrophotgraphic drum 28, and an electrophographic cartridge 21 in accordance with selected embodiments of the present invention. The electrophotographic cartridge 21 typically comprises an electrophotographic photoreceptor 29 and a charging device 25 that charges the electrophotographic photoreceptor 29, a developing device 24 which develops an electrostatic latent image formed on the electrophotographic photoreceptor 29, and a cleaning device 26 which cleans a surface of the electrophotographic photoreceptor 29. The electrophotographic cartridge 21 may be attached to or detached from the image forming apparatus 30, and the electrophotographic photoreceptor 29 is described more fully above.

The electrophotographic photoreceptor drum 28, 29 for an image forming apparatus 30, generally includes a drum 28 that is attachable to and detachable from the electrophotographic apparatus 30 and that includes an electrophotographic photoreceptor 29 disposed on the drum 28, wherein the electrophotographic photoreceptor 29 is described more fully above.

Generally, the image forming apparatus 30 includes a photoreceptor unit (e.g., an electrophotographic photoreceptor drum 28, 29), a charging device 25 which charges the photoreceptor unit, an imagewise light irradiating device 22 which irradiates the charged photoreceptor unit with imagewise light to form an electrostatic latent image on the photoreceptor unit, a developing unit 24 that develops the electrostatic latent image with a toner to form a toner image on the photoreceptor unit, and a transfer device 27 which transfers the toner image onto a receiving material, such as paper P, wherein the photoreceptor unit comprises an electrophotographic photoreceptor 29 as described in greater detail above. The charging device 25 may be supplied with a voltage as a charging unit and may contact and charge the electrophotographic receptor. Where desired, the apparatus may include a pre-exposure unit 23 to erase residual charge on the surface of the electrophotographic photoreceptor to prepare for a next cycle.

Where desired, the photoreceptor may have a protective layer disposed thereon (not shown).

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A naphthoquinone derivative represented by Formula 1:

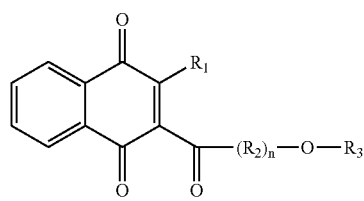

Formula 1 wherein:
$R_1$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms;

$R_2$ is selected from the group consisting of an alkylene group having 2 to 20 carbon atoms, an arylene group having 6 to 30 carbon atoms, and an arylene-alkylene group having 7 to 30 carbon atoms;

n is 1; and $R_3$ is selected from the group consisting of a substituted or unsubstituted alkyl group having 1 to 20 carbon atoms, a substituted or unsubstituted aryl group having 6 to 30 carbon atoms, a substituted or unsubstituted aralkyl group having 7 to 30 carbon atoms, and a group represented by Formula 1a or 1b:

 Formula 1a

 Formula 1b wherein:
$R_4$, $R_5$, and $R_6$ are selected from the group consisting of, independently, an alkylene group having 2 to 20 carbon atoms, an arylene group having 6 to 30 carbon atoms, and an arylene-alkylene group having 7 to 30 carbon atoms; and $R_7$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms.

2. The naphthoquinone derivative according to claim 1, wherein $R_2$ is a phenylene group and $R_3$ is a methyl group.

3. The naphthoquinone derivative according to claim 1, wherein $R_3$ is —$R_4$—O—$R_7$ of the Formula 1a, $R_4$ is an ethylene group, and $R_7$ is selected from the group consisting of a tert-butyl, a phenyl, a benzyl, a 4-nitrophenyl, an isopropyl, an ethyl, a 4-tert-butylphenyl, and a 4-nitrophenylmethyl group.

4. The naphthoquinone derivative according to claim 1, wherein $R_3$ is —$R_4$—O—$R_7$ of the Formula 1a, $R_4$ is a phenylene group, and $R_7$ is a butyl group.

5. The naphthoquinone derivative according to claim 1, wherein $R_3$ is —$R_4$—O—$R_7$ of the Formula 1a, $R_4$ is a methylene-phenylene group, and $R_7$ is selected from the group consisting of —$CH(CH_3)CH(CH_3)_2$, —$CH_2CH(C_2H_5)(CH_2)_3CH_3$, a methyl group, and an isopropyl group.

6. The naphthoquinone derivative according to claim 1, wherein $R_3$ is —$R_4$—O—$R_7$ of the Formula 1a, $R_4$ is an ethylene-phenylene group, and $R_7$ is an n-butyl group.

7. An electrophotographic photoreceptor comprising:
a substrate; and
a photosensitive layer comprising a naphthoquinone derivative represented by Formula 1:

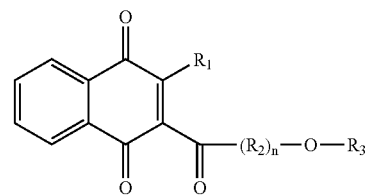

Formula 1 wherein:
$R_1$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms;

$R_2$ is selected from the group consisting of an alkylene group having 2 to 20 carbon atoms, an arylene group having 6 to 30 carbon atoms, and an arylene-alkylene group having 7 to 30 carbon atoms;

n is 1; and $R_3$ is selected from the group consisting of a substituted or unsubstituted alkyl group having 1 to 20 carbon atoms, a substituted or unsubstituted aryl group having 6 to 30 carbon atoms, a substituted or unsubstituted aralkyl group having 7 to 30 carbon atoms, and a group represented by Formula 1a or 1b:

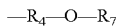
$\quad -R_4-O-R_7 \quad$ Formula 1a

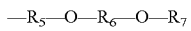
$\quad -R_5-O-R_6-O-R_7 \quad$ Formula 1b wherein:

$R_4$, $R_5$, and $R_6$ are selected from the group consisting of, independently, an alkylene group having 2 to 20 carbon atoms, an arylene group having 6 to 30 carbon atoms, and an arylene-alkylene group having 7 to 30 carbon atoms; and $R_7$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms.

8. The electrophotographic photoreceptor according to claim 7, wherein $R_2$ is a phenylene group and $R_3$ is a methyl group.

9. The electrophotographic photoreceptor according to claim 7, wherein $R_3$ is $-R_4-O-R_7$ of the Formula 1a, $R_4$ is an ethylene group, and $R_7$ is selected from the group consisting of a tert-butyl, a phenyl, a benzyl, a 4-nitrophenyl, an isopropyl, an ethyl, a 4-tert-butylphenyl, and a 4-nitrophenylmethyl group.

10. The electrophotographic photoreceptor according to claim 7, wherein $R_3$ is $-R_4-O-R_7$ of the Formula 1a, $R_4$ is a phenylene group, and $R_7$ is a butyl group.

11. The electrophotographic photoreceptor according to claim 7, wherein $R_3$ is $-R_4-O-R_7$ of the Formula 1a, $R_4$ is a methylene-phenylene group, and $R_7$ is selected from the group consisting of $-CH(CH_3)CH(CH_3)_2$, $-CH_2CH(C_2H_5)(CH_2)_3CH_3$, a methyl group, and an isopropyl group.

12. The electrophotographic photoreceptor according to claim 7, wherein $R_3$ is $-R_4-O-R_7$ of the Formula 1a, $R_4$ is an ethylene-phenylene group, and $R_7$ is an n-butyl group.

13. An electrophotographic drum, comprising:
a drum;
a substrate disposed on the drum; and
an electrophotographic photoreceptor disposed on the substrate, the electrophotographic photoreceptor comprising:
a substrate; and
a photosensitive layer comprising a naphthoquinone derivative represented by Formula 1:

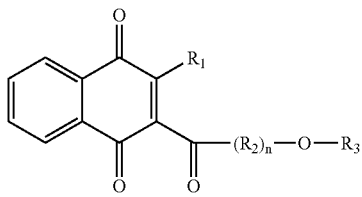

Formula 1 wherein:

$R_1$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms;

$R_2$ is selected from the group consisting of an alkylene group having 2 to 20 carbon atoms, an arylene group having 6 to 30 carbon atoms, and an arylene-alkylene group having 7 to 30 carbon atoms;

n is 1; and $R_3$ is selected from the group consisting of a substituted or unsubstituted alkyl group having 1 to 20 carbon atoms, a substituted or unsubstituted aryl group having 6 to 30 carbon atoms, a substituted or unsubstituted aralkyl group having 7 to 30 carbon atoms, and a group represented by Formula 1a or 1b:

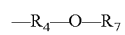
$\quad -R_4-O-R_7 \quad$ Formula 1a

$\quad -R_5-O-R_6-O-R_7 \quad$ Formula 1b wherein:

$R_4$, $R_5$, and $R_6$ are selected from the group consisting of, independently, an alkylene group having 2 to 20 carbon atoms, an arylene group having 6 to 30 carbon atoms, and an arylene-alkylene group having 7 to 30 carbon atoms; and $R_7$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms, wherein the electrophotographic drum is attachable to/detachable from an image forming apparatus.

14. The electrophotographic drum according to claim 13, wherein $R_2$ is a phenylene group and $R_3$ is a methyl group.

15. The electrophotographic drum according to claim 13, wherein $R_3$ is $-R_4-O-R_7$ of the Formula 1a, $R_4$ is an ethylene group, and $R_7$ is selected from the group consisting of a tert-butyl, a phenyl, a benzyl, a 4-nitrophenyl, an isopropyl, an ethyl, a 4-tert-butylphenyl, and a 4-nitrophenylmethyl group.

16. The electrophotographic drum according to claim 13, wherein $R_3$ is $-R_4-O-R_7$ of the Formula 1a, $R_4$ is a phenylene group, and $R_7$ is a butyl group.

17. The electrophotographic drum according to claim 13, wherein $R_3$ is $-R_4-O-R_7$ of the Formula 1a, $R_4$ is a methylene-phenylene group, and $R_7$ is selected from the group consisting of $-CH(CH_3)CH(CH_3)_2$, $-CH_2CH(C_2H_5)(CH_2)_3CH_3$, a methyl group, and an isopropyl group.

18. The electrophotographic drum according to claim 13, wherein $R_3$ is $-R_4-O-R_7$ of the Formula 1a, $R_4$ is an ethylene-phenylene group, and $R_7$ is an n-butyl group.

19. An electrophotographic cartridge, comprising:
an electrophotographic photoreceptor comprising:
a substrate; and
a photosensitive layer comprising a naphthoquinone derivative represented by Formula 1:

Formula 1

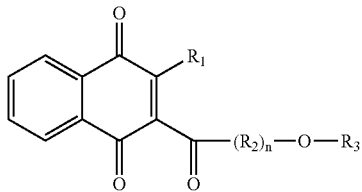

wherein:
- $R_1$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms;
- $R_2$ is selected from the group consisting of an alkylene group having 2 to 20 carbon atoms, an arylene group having 6 to 30 carbon atoms, and an arylene-alkylene group having 7 to 30 carbon atoms;
- n is 1; and
- $R_3$ is selected from the group consisting of a substituted or unsubstituted alkyl group having 1 to 20 carbon atoms, a substituted or unsubstituted aryl group having 6 to 30 carbon atoms, a substituted or unsubstituted aralkyl group having 7 to 30 carbon atoms, and a group represented by Formula 1a or 1b:

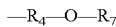      Formula 1a

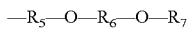      Formula 1b wherein:
- $R_4$, $R_5$, and $R_6$ are selected from the group consisting of, independently, an alkylene group having 2 to 20 carbon atoms, an arylene group having 6 to 30 carbon atoms, and an arylene-alkylene group having 7 to 30 carbon atoms; and
- $R_7$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms.

20. The electrophotographic cartridge according to claim 19, wherein $R_2$ is a phenylene group and $R_3$ is a methyl group.

21. The electrophotographic cartridge according to claim 19, wherein $R_3$ is —$R_4$—O—$R_7$ of the Formula 1a, $R_4$ is an ethylene group, and $R_7$ is selected from the group consisting of a tert-butyl, a phenyl, a benzyl, a 4-nitrophenyl, an isopropyl, an ethyl, a 4-tert-butylphenyl, and a 4-nitrophenylmethyl group.

22. The electrophotographic cartridge according to claim 19, wherein $R_3$ is —$R_4$—O—$R_7$ of the Formula 1a, $R_4$ is a phenylene group, and $R_7$ is a butyl group.

23. The electrophotographic cartridge according to claim 19, wherein $R_3$ is —$R_4$—O—$R_7$ of the Formula 1a, $R_4$ is a methylene-phenylene group, and $R_7$ is selected from the group consisting of —CH($CH_3$)CH($CH_3$)$_2$, —$CH_2$CH($C_2H_5$)($CH_2$)$_3$$CH_3$, a methyl group, and an isopropyl group.

24. The electrophotographic cartridge according to claim 19, wherein $R_3$ is —$R_4$—O—$R_7$ of the Formula 1a, $R_4$ is an ethylene-phenylene group, and $R_7$ is an n-butyl group.

25. An image forming apparatus, comprising:
- a photoconductor unit having an electrophotographic photoreceptor, the electrophotograpohic photoconductor comprising:
- a substrate; and
- a photosensitive layer comprising a naphthoquinone derivative represented by Formula 1:

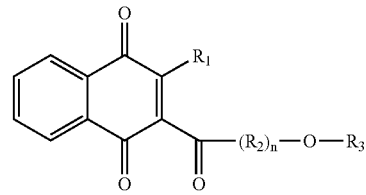

Formula 1 wherein:
- $R_1$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms;
- $R_2$ is selected from the group consisting of an alkylene group having 2 to 20 carbon atoms, an arylene group having 6 to 30 carbon atoms, and an arylene-alkylene group having 7 to 30 carbon atoms;
- n is 1; and
- $R_3$ is selected from the group consisting of a substituted or unsubstituted alkyl group having 1 to 20 carbon atoms, a substituted or unsubstituted aryl group having 6 to 30 carbon atoms, a substituted or unsubstituted aralkyl group having 7 to 30 carbon atoms, and a group represented by Formula 1a or 1b:

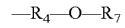      Formula 1a

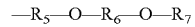      Formula 1b wherein:
- $R_4$, $R_5$, and $R_6$ are selected from the group consisting of, independently, an alkylene group having 2 to 20 carbon atoms, an arylene group having 6 to 30 carbon atoms, and an arylene-alkylene group having 7 to 30 carbon atoms; and
- $R_7$ is selected from the group consisting of a substituted or unsubstituted alkyl group having 1 to 20 carbon atoms, a substituted or unsubstituted aryl group having 6 to 30 carbon atoms, and a substituted or unsubstituted aralkyl group having 7 to 30 carbon atoms,
- a charging device which charges the photoconductor unit;
- an imagewise light irradiating device which irradiates the charged photoconductor unit with imagewise light to form an electrostatic latent image on the photoconductor unit;
- a developing unit that develops the electrostatic latent image with a toner to form a toner image on the photoconductor unit; and
- a transfer device which transfers the toner image onto a receiving material.

26. The image forming apparatus according to claim 25, wherein $R_2$ is a phenylene group and $R_3$ is a methyl group.

27. The image forming apparatus according to claim 25, wherein $R_3$ is —$R_4$—O—$R_7$ of the Formula 1a, $R_4$ is an ethylene group, and $R_7$ is selected from the group consisting of a tert-butyl, a phenyl, a benzyl, a 4-nitrophenyl, an isopropyl, an ethyl, a 4-tert-butylphenyl, and a 4-nitrophenylmethyl group.

28. The image forming apparatus according to claim 25, wherein $R_3$ is —$R_4$—O—$R_7$ of the Formula 1a, $R_4$ is a phenylene group, and $R_7$ is a butyl group.

29. The image forming apparatus according to claim 25, wherein $R_3$ is —$R_4$—O—$R_7$ of the Formula 1a, $R_4$ is a methylene-phenylene group, and $R_7$ is selected from the group consisting of —CH(CH$_3$)CH(CH$_3$)$_2$, —CH$_2$CH(C$_2$H$_5$)(CH$_2$)$_3$CH$_3$, a methyl group, and an isopropyl group.

30. The image forming apparatus according to claim 25, wherein $R_3$ is —$R_4$—O—$R_7$ of the Formula 1a, $R_4$ is an ethylene-phenylene group, and $R_7$ is an n-butyl group.

* * * * *